(12) United States Patent
Masuda et al.

(10) Patent No.: US 6,846,299 B2
(45) Date of Patent: Jan. 25, 2005

(54) METHOD FOR CONTINUOUS RECIRCULATING PERITONEAL DIALYSIS

(75) Inventors: Toshiaki Masuda, Osaka (JP); Hidetoshi Yamamoto, Osaka (JP)

(73) Assignee: Nipro Corporation, Osaka (JP)

(*) Notice: Subject to any disclaimer, the term of this patent is extended or adjusted under 35 U.S.C. 154(b) by 17 days.

(21) Appl. No.: 10/171,655

(22) Filed: Jun. 17, 2002

(65) Prior Publication Data

US 2002/0187940 A1 Dec. 12, 2002

Related U.S. Application Data

(62) Division of application No. 09/334,893, filed on Jun. 17, 1999, now Pat. No. 6,429,294.

(30) Foreign Application Priority Data

Jun. 17, 1998 (JP) ............................. 10-170282

(51) Int. Cl.⁷ .............................. A61M 1/14; A61M 1/28
(52) U.S. Cl. .......................... 604/29; 604/30; 530/362; 530/363; 514/21; 436/74; 436/79
(58) Field of Search ..................... 604/29, 30; 530/362, 530/363; 514/21; 436/74, 79

(56) References Cited

U.S. PATENT DOCUMENTS

| | | | |
|---|---|---|---|
| 4,338,190 A | 7/1982 | Kraus et al. | 210/195.2 |
| 4,339,433 A | 7/1982 | Kartinos et al. | 424/78 |
| 4,604,379 A | 8/1986 | Twardowski et al. | 514/21 |
| 4,618,343 A | 10/1986 | Polaschegg | 604/29 |
| 4,886,789 A | 12/1989 | Milner | 514/60 |
| 5,141,493 A | 8/1992 | Jacobsen et al. | 604/29 |
| 5,436,232 A | 7/1995 | Förster et al. | 514/60 |
| 5,641,405 A | 6/1997 | Keshaviah et al. | 210/645 |

FOREIGN PATENT DOCUMENTS

| | | |
|---|---|---|
| EP | 0 207 676 A2 | 1/1987 |
| EP | 0 928 615 A1 | 7/1999 |
| WO | WO-97/47337 | * 12/1997 |

OTHER PUBLICATIONS

Carlsson et al., "In vivo inhibition of transcellular . . . ", *Am. J Physiol*, 271 (6 Pt 2):H2254–62 Dec. 1996, at (http://www/infotrieve.com/freemedline/cg...).

Park et al., "Albumin–based Solutions for Peritoneal Dialysis: Investigations . . . ", *Artificial Organs*, 19(4):307–314, 1995.

* cited by examiner

*Primary Examiner*—Jon Weber
*Assistant Examiner*—Chih-Min Kam
(74) *Attorney, Agent, or Firm*—Kubovcik & Kubovcik

(57) ABSTRACT

Method for a continuous recirculating peritoneal dialysis wherein the peritoneal dialysis fluid is infused into a peritoneal cavity of a patient and then, typically on a continuous process basis a portion of the dialysis fluid is sequentially drained from the cavity, cleansed through an extracorpreal dialyzer, and reinfused into the cavity. The dialysis fluid contains as an osmotic agent a substance which does not substantially permeate through pores of hollow fiber membrane of an extracorporeal dialyzer, preferably an osmotic agent having a molecular weight of about 20,000 to about 100,000. The supplemented amount of the osmotic agent is reduced or not needed during the dialysis.

6 Claims, 3 Drawing Sheets

METHOD FOR CONTINUOUS RECIRCULATING PERITONEAL DIALYSIS

This application is a division of application Ser. No. 09/334,893, filed Jun. 17, 1999, now U.S. Pat. No 6,429,294.

FIELD OF THE INVENTION

The present invention relates to a peritoneal dialysis fluid used for continuous recirculating peritoneal dialysis and a method for said dialysis, wherein the peritoneal dialysis fluid is infused into a peritoneal cavity and then, typically on a continuous process basis, a portion of the dialysis fluid is sequentially drained from the cavity, cleansed through an extracorporeal dialyzer, and reinfused into the cavity.

BACKGROUND OF THE INVENTION

The normal function of the mammalian kidney includes such activity as maintaining a constant acid-base and electrolyte balance, removing excess fluids and removing undesirable products of the body's metabolism from the blood. Heretofore, dialysis methods such as hemodialysis and peritoneal dialysis have been practiced on patients whose kidney function was reduced. Here, in hemodialysis, the blood is withdrawn from the patient's bloodstream and passed through a dialyzer wherein the blood is brought into contact with a selectively permeable membrane made, for example, of cellulosic acetate, the remote side of which contacts a dialysis fluid. By a principle of diffusion, solutes in the blood are transported across the membrane into the dialysis fluid and water is removed by ultrafiltration. The treatment is normally carried out in the out-patient department of hospitals but causes patients to be retained in the hospital for a long time.

Peritoneal dialysis is now a well-established procedure which may be substituted for extacorporeal hemodialysis and has an it advantage in that patients do not have to be treated in hospitals and the procedure can be carried out at home. The conventional peritoneal dialysis comprises introducing a fresh peritoneal dialysis fluid into a peritoneal cavity in the abdomen of the patient, allowing the fluid to remain there for several hours, dialyzing the fluids through a peritoneum as a semi-permeable membrane, and then draining the dialysis fluid containing metabolic waste products from the peritoneal cavity. However, this procedure has disadvantages including the problem and danger of peritonitis, a lower efficiency than hemodialysis which requires a longer treatment or process time with large volumes of solution and a high cost of commercially prepared dialysate solution.

Accordingly, in order to increase the efficiency of peritoneal dialysis, a number of improved peritoneal dialyses have been known.

In U.S. Pat. No. 5,141,493 there is disclosed a peritoneal dialysis system which comprises connection means for carrying a primary solution that is a peritoneal dialysis fluid from a primary circuit means to a peritoneal cavity of a patient, withdrawing at least some solution from the patient into the primary circuit means, wherein the primary circuit means has a reversible pump for circulating the primary solution, and a dialyzer to enable removal of waste products from the primary solution to a secondary solution that is a dialysate for hemodialysis. The peritoneal dialysis fluid withdrawn from the peritoneal cavity of the patient is purified sequentially with said dialysate through the dialyzer and returned again into the cavity of the patient.

In U.S. Pat. No. 5,641,405 there is disclosed a system including only one pump for providing a peritoneal dialysis fluid into and out of a patient. This system comprises a single catheter, a source of peritoneal dialysis fluid, a dialyzer and a single reversible pump positioned between the source of peritoneal dialysis fluid and the catheter. In this arrangement, the peritoneal dialysis fluid is passed from the source of peritoneal dialysis fluid through the dialyzer to be dialyzed before reaching the catheter and pumped out of the peritoneal cavity of the patient to the source of dialysis fluid and temporarily pooled in the source, and then passed through the dialyzer again and returned to the peritoneal cavity of the patient.

The peritoneal dialysis fluid used in the above-described two peritoneal dialysis systems contains glucose as an osmotic agent. Solutes such as urea and creatinine diffuse from the blood in capillaries of the peritoneum into the dialysis fluid due to the presence of a diffusion gradient. Also the presence of an osmotic gradient due to glucose between the peritoneal cavity and the blood causes excess water removal from the blood in the peritoneal capillaries into the dialysis fluid which is then drained outside the abdomen of the patient. However, glucose in the dialysis fluid permeates through the hollow fiber membrane of the extracorporeal dialyzer to be readily taken up into a dialysate as cleaning solution because the separation limitation of the membrane is approximately 5,000 to 10,000 daltons. Accordingly, there is a problem that in order to maintain the osmotic gradient which is a water-removing ability of the peritoneal dialysis fluid, glucose must be supplied into the fluid during the peritoneal dialysis using a glucose injector, etc. As for the usage of glucose, for example, when the peritoneal dialysis fluid is circulated at a flow rate of 0.1 liter/minute for 6 hours, while maintaining an osmotic pressure of 1.5% dialysis fluid, 15 g of glucose is contained in one liter of dialysis fluid : Daianeal 1.5 (trade name, manufactured by Baxter), a huge amount of glucose is necessary as shown by the following formula.

$$0.1(\text{liter}) \times 60(\text{min}) \times 6(\text{h}) \times 15(\text{g}) = 540(\text{g})$$

SUMMARY OF THE INVENTION

The present invention is made under the above-described circumstances and has for its object to enable efficient peritoneal dialysis and provide a peritoneal dialysis fluid that is cost-competitive.

In order to solve the above-described problem, the present inventors have made intensive research. As a result, it has been found that addition of an osmotic agent that does not substantially permeate pores of a hollow fiber membrane of a dialyzer enables efficient peritoneal dialysis, and gives a peritoneal dialysis fluid that is cost-competitive.

That is, the present invention relates to a peritoneal dialysis fluid used for a continuous recirculating peritoneal dialysis which comprises as an osmotic agent a substance which does not substantially permeate through pores of a hollow fiber membrane of an extracorporeal dialyzer.

The present invention also provides a method for a continuous recirculating peritoneal dialysis which comprises i) infusing a peritoneal dialysis fluid in a peritoneal cavity, the fluid comprising as an osmotic agent a substance which does not substantially permeate through pores of a hollow fiber membrane of an extracorporeal dialyzer, ii) sequentially draining the peritoneal dialysis fluid out of the peritoneal cavity, iii) cleansing the peritoneal dialysis fluid through an extracorporeal dialyzer, and iv) reinfusing the cleansed peritoneal dialysis fluid into the peritoneal cavity.

DETAILED DESCRIPTION OF THE INVENTION

Figure 1:
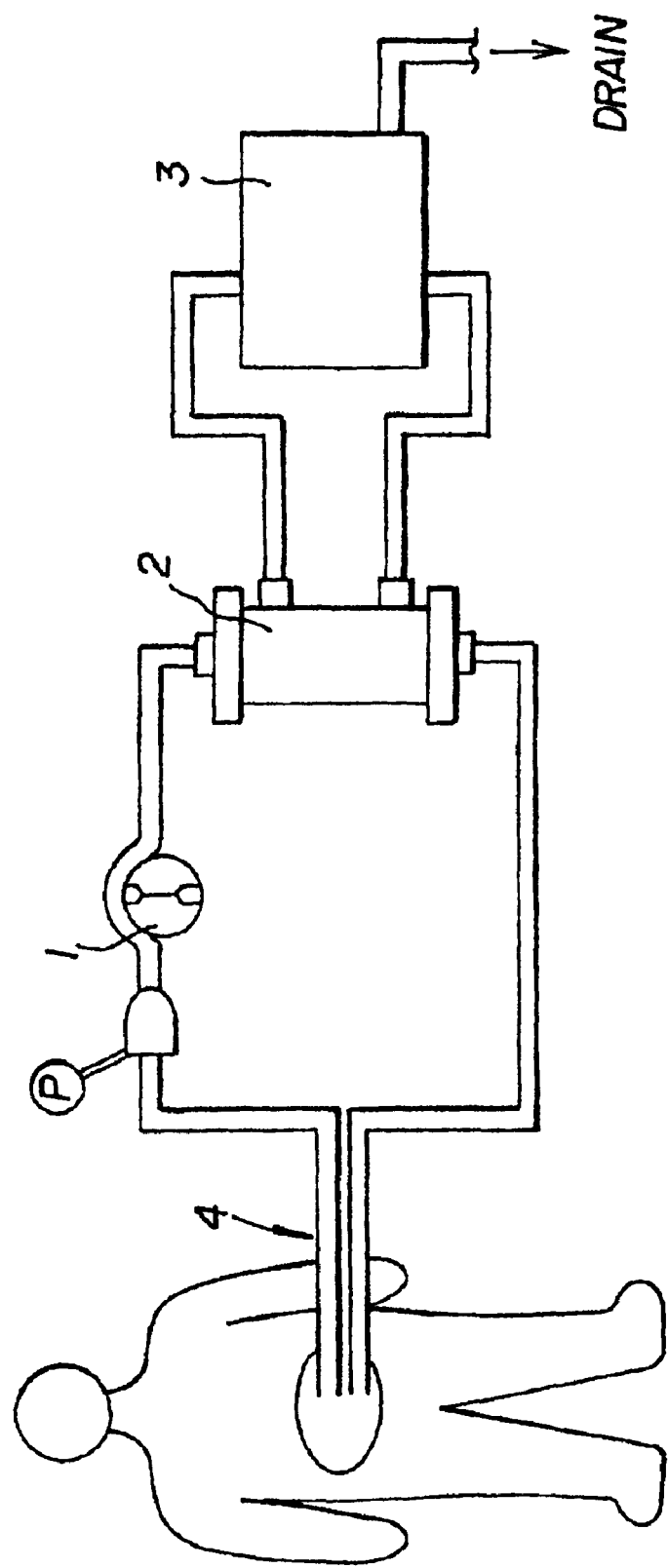
FIG. 1 shows a scheme of continuous recirculating peritoneal dialysis.

Here, a petironeal dialysis fluid is a solution to remove solutes and excess water from the blood in the peritoneal cavity by diffusion and ultrafiltration across the peritoneum which is a semi-permeable membrane, and usually comprises at least an osmotic agent, electrolytes and pH adjusting agent.

The osmotic agent in the present invention is a substance which does not substantially permeate through pores of a hollow fiber membrane of a dialyzer. Said osmotic agent has a molecular weight of about 20,000 to about 100,000, preferably about 30,000 to about 80,000 because a separation limitation of the hollow fiber membrane is ordinarily about 5,000 to about 10,000 daltons. The general concentration of the osmotic agent in the peritoneal dialysis fluid is sufficient to provide an osmotic pressure so as to allow removal of solutes and excess water in the peritoneum but is not generally limited in the present invention.

The osmotic agent is preferably at least one compound selected from the group consisting of albumin, a glucose polymer and dextran. Particularly, albumin is preferred. The albumin comprises human serum albumin, preferably genetically engineered albumin. The concentration of albumin in the peritoneal dialysis fluid is preferably about 20 to about 250 g/L, most preferably about 70 to about 150 g/L, which is sufficient to provide an osmotic gradient similar to that due to glucose in a conventional dialysis fluid. An amount of less than 20 g/L of albumin exhibits an insufficient water-removal efficiency while an amount of more than 250 g/L of albumin results in excess osmotic pressure which is undesirable for a patient's body. The peritoneal dialysis fluid may contain sodium N-acetyltryptophan, sodium caprylate, etc., as an albumin stabilizer.

Glucose polymer has preferably a molecular weight of about 30,000 to about 80,000 and is exemplified as partially hydrolyzed dextran having a molecular weight of about 75,000.

The osmotic agent can be obtained by substituting partly or entirely for glucose with an osmotic agent according to the present invention such as albumin, a glucose polymer, or dextran so as to maintain the osmotic gradient of the conventionally used peritoneal dialysis fluid.

The peritoneal dialysis fluid of the present invention contains a sufficient amount of the effective osmotic agent, in addition to physiologically acceptable salts, to impart generally to the fluid a total osmolality of from about 200 to about 600; preferably about 300 to about 500 mOsm/Kg.

The pH of a peritoneal dialysis fluid of the present invention is generally from about 4.5 to 7.5.

As the composition of the peritoneal dialysis fluid of the present invention, various compositions with different osmotic pressures may be adopted depending on the symptom of patients. The electrolytes may contain positive ions such as alkali metal ions, alkaline earth metal ions, etc., and negative ions such as chloride ion, etc. Alkali metal ions include sodium, potassium, etc., and alkaline earth metal ions include calcium, magnesiuln, etc. The amount of positive ions can be generally 110 to 140 mEq/L of sodium ion, 0 to 2.5 mEq/L of potassium ion, 0 to 3 mEq/L of magnesium ion and 0 to 6 mEq/L of calcium ion. Preferably, the amount of chloride ion is 80 to 144 mEq/L.

When albumin is used as an osmotic agent, an example of the composition contains 132 mEq/l of Na, 3.5 mEq/l of Ca, 1.5 mEq/l of Mg, 102 mEq of Cl, 35 mEq/l of lactic acid, and 5.7 g/dl of albumin, or 132 mEq/l of Na, 3.5 mEq/l of Ca, 1.5 mEq/l of Mg, 102 mEq of Cl, 35 mEq/l of lactic acid, and 9.6 g/dl of albumin.

The peritoneal dialysis fluid of the present invention is preferably regulated by pH adjusting agents such as inorganic acids, organic acids, alkali substances, etc. in a pharmaceutically stable range. Inorganic acids include hydrochloric acid, etc., organic acids include lactic acid, malic acid, acetic acid, succinic acid, maleic acid, pyruvic acid, citric acid, etc., and alkali substances include sodium hydrate, sodium bicarbonate, etc.

In one embodiment, the peritoneal dialysis fluid of the present invention has a pH of from about 4.5 to about 7.5 and a total osmolality of from about 300 to about 500 mOsm/Kg, said dialysis fluid comprising;

i) an osmotic agent which comprises an albumin in an amount of from about 20 to about 250 g/L, ii) electrolytes and iii) pH adjusting agent.

In another embodiment, the peritoneal dialysis fluid used for a continuous recirculating peritoneal dialysis comprises albumin of about 70 to about 150 g/L, sodium ions of about 130 to about 140 mEq/L, calcium ions of about 3.0 to about 4.5 mEq/L, magnesium ions of about 0.5 to about 2.0 mEq/L, chloride ions of about 95 to about 110 mEq/L, and lactate ions of about 35 to about 40 mEq/L.

As a detergent solution for the peritoneal dialysis fluid withdrawn from the peritoneal cavity, a dialysate which is usually used in hemodialysis is preferably adopted. The detergent solution typically includes the following components;

sodium ions of about 130 to about 145 mEq/L, potassium ions of about 2.0 to about 2.5 mEq/L, calcium ions of about 2.5 to about 4.0 mEq/L, magnesium ions of about 1.0 to about 1.5 mEq/L, chloride ions of about 95 to about 200 mEq/L, bicarbonate ions of about 25 to about 30 mEq/L, and glucose of about 90 to about 200 g/L.

For example, concentrates for haemodialysis such as KINDARY™ (manufactured by Fuso Pharmaceutical Industries Co., Ltd.), and SOLITA™ (manufactured by Shimizu Pharmaceutical Co., Ltd.), and powders such as LYMPAK™ (Nipro Co., Ltd.) are dissolved in RO (reverse osmosis) water in a detergent solution supplying apparatus.

The method for dialyzing a peritoneum of the present invention includes conventional peritoneal dialysis such as an intermittent peritoneal dialysis (IPD), a continuous ambulatory peritoneal dialysis (CAPD) and a continuous cyclic peritoneal dialysis (CCPD). A dialyzer is equipped with the conventional apparatus of these methods.

The peritoneal dialysis fluid drained from the peritoneal cavity is passed through the dialyzer to remove the waste products in said dialysis fluid and then the cleansed fluid is returned into the peritoneal cavity. If necessarily, the steps which comprise removing the fluid from the peritoneum, passing the fluid through the dialyzer, and reinfusing the cleansed fluid into the peritoneum are repeated.

A method for dialyzing a patient in the present invention comprises (a) placing a fluid pathway in a peritoneal cavity in the abdomen of the patient, (b) infusing a peritoneal dialysis fluid comprising as an osmotic agent a substance which does not substantially permeate through pores of a hollow fiber membrane of an extracorporeal dialyzer into a peritoneal cavity, (c) maintaining a substantially effective osmotic pressure of the peritoneal dialysis fluid in the peritoneal cavity, (d) transferring said peritoneal dialysis fluid to the dialyzer which consists of hollow fiber membranes, (e) cleansing the transferred peritoneal dialysis fluid in the dialyzer using a detergent solution and (f) reinfusing the cleansed peritoneal dialysis fluid into the peritoneum.

The apparatus used for the method of the present invention includes ordinarily a liquid pathway into the peritoneal cavity, pump(s), dialyzer, source of dialysis fluid and an apparatus for it waste liquid etc.

The liquid pathway usually comprises a dialysis catheter, single lumen catheter or double lumen catheter for peritoneal dialysis. The source of dialysis fluid, for example, dialysis fluid bag, and external dialyzing means, for example, so called dialyzer, are connected with said liquid pathway.

The dialysis fluid is infused into the peritoneal cavity by using a pump or natural gravity. The draining of the dialysis fluid from the peritoneal cavity is carried out also using a pump or natural gravity. It is preferable to infuse or drain the dialysis fluid into or out of the peritoneum with controlled velocity. An initial volume of the infused fluid depends on the contents of the osmotic agents and the substances which influence the osmotic pressure in the peritoneal dialysis. Although the initial volume has to be changed by factors such as a patient's size, level of kidney function, meals of the patient, or metabolic ability, it is generally about 0.5 to about 2.5 L per patient.

An osmotic gradient in the dialysis fluid causes removing of excess water in the peritoneal cavity continuously and maintains substantially fixed osmolality of the dialysis fluid during at least 6 to 24 hours, which is usually 200 to 600 mOsm/Kg, preferably about 300 to about 500 mOsm/Kg. While water is transferred through the peritoneum and diluted into the dialysis fluid during the peritoneal dialysis, osmotic agent is gradually released to maintain a certain concentration in the dialysis fluid. The dialysis fluid is drained from the peritoneal cavity, cleansed with a detergent solution in the dialyzer and reinfused into the peritoneum, and these steps are repeated if desired.

An osmotic agent such as glucose is necessary to be supplemented to a conventional peritoneal dialysis fluid according to change of the osmotic pressure in the peritoneal cavity. However, the dialysis fluid in the present invention is not required to be supplemented with an osmotic agent or otherwise is required to be supplemented with only a small amount of the osmotic agent.

The drained dialysis fluid is passed through the dialyzer in order to be purified, and infused again into the peritoneal cavity via the liquid pathway. The loss of osmotic agent is supplemented occasionally according to the concentration of the osmotic agent in the drained dialysis fluid, which is determined by a usual measurement.

The extracorporeal dialyzer comprises a housing for encasing a large amount of hollow fiber membranes as a bundle and allows appropriate entry and exit of the peritoneal dialysis fluid. Both ends of the bundle are supported with a segregation wall which is made of synthetic high molecular weight substance and adhered. The segregation walls are packed in the ends of the casing. The opening parts of the hollow fiber membranes in the bundle are faced towards the outer ends of the segregation walls. The inlet and outlet of the detergent solution are provided with the housing. The drained dialysis fluid is introduced into and removed out of an inside of the hollow fiber membranes while the detergent solution is passed into and out of the remote side of hollow fiber membranes in the external dialyzer. The dialysis is carried out by contacting the peritoneal dialysis fluid with the detergent solution through the hollow fiber membranes to remove the undesirable products from the dialysis fluid. The cleansing of the dialysis fluid enables dialyzing of the peritoneum typically on a continuous process basis. The detergent solution is prepared by mixing the dialysate with RO (reverse osmosis) water in a cleansing supplying apparatus and supplied into the dialyzer via a circulating line of the detergent solution. The detergent solution is optionally a solution such as the above mentioned dialysate from which unnecessary components such as glucose are excluded.

As examples of hollow fiber membranes, there are membranes made of cellulosic materials such as cellulose acetate, CUPROPHAN™ (copper ammonium rayon) and synthetic high molecular weight substances such as polyacrylonitrile, polymethacrylate, ethylene-vinyl alcohol, polysulfone and polyamide. The separation limitation, that is cut-off point is preferably a molecular weight of about 2,000 to about 70,000 daltons, most preferably, about 5,000 to about 10,000 daltons. The hollow fiber having such separation limitation enables an invasion of bacteria through the membrane into the dialysis fluid to be avoided. As this separation limitation is smaller than the molecule of albumin, an osmotic agent such as albumin is not removed from the dialysis fluid.

A reversible pump is provided with a dialysis line and a pooling bag of the peritoneal dialysis fluid is provided with the end of the dialysis line, and therefore, the dialysis fluid may be transported between the peritoneum and said pooling bag.

Figure 3:
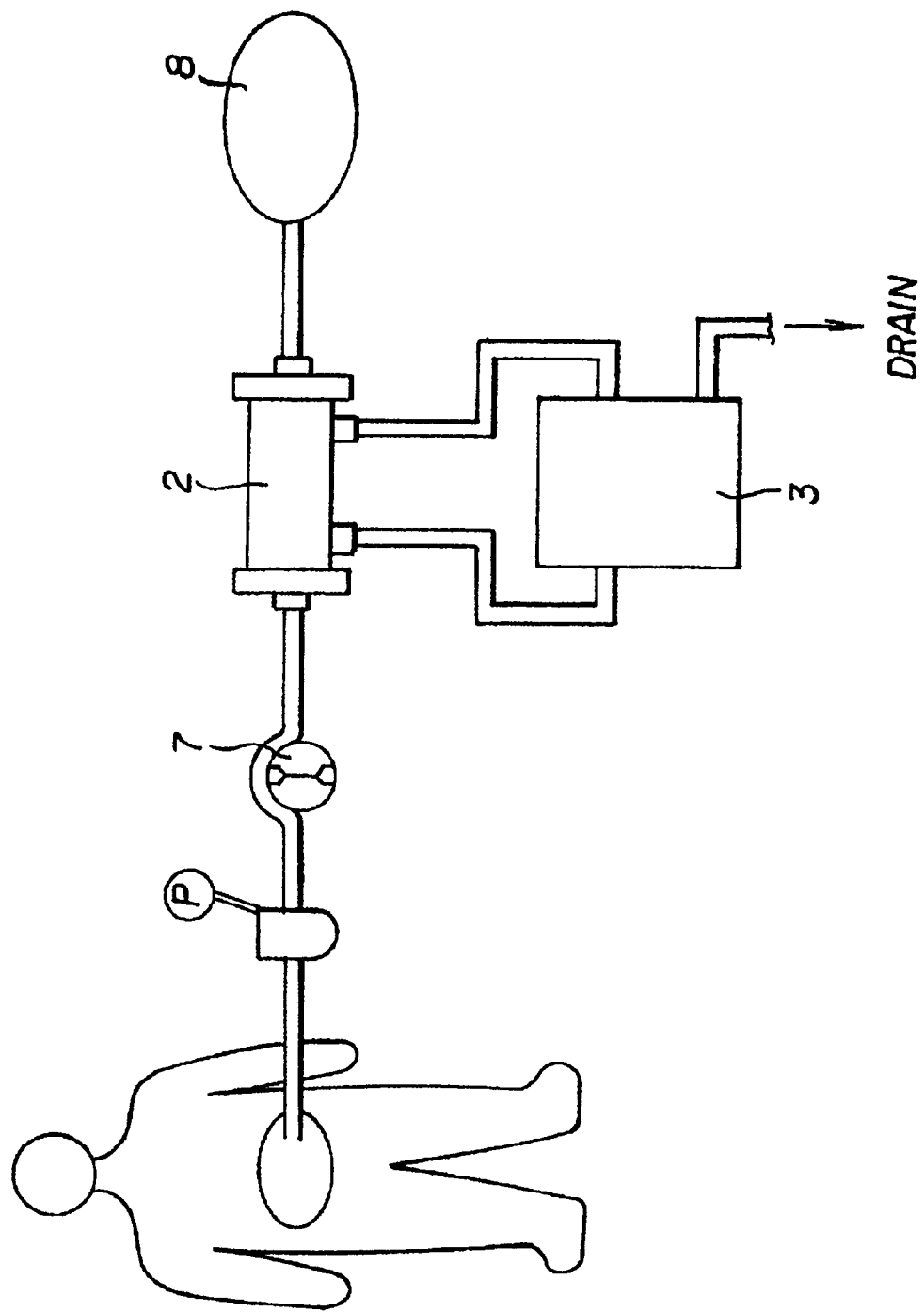
FIG. 3 show another scheme of continuous recirculating peritoneal dialysis.

The system used for the present invention is exemplified in FIGS. 3, 4, or 7 of U.S. Pat. No. 5,641,405 but is not limited to these figures.

The method for dialyzing a patient using the peritoneal dialysis fluid of the present invention comprises (a) placing a fluid pathway such as a catheter in a peritoneal cavity of the patient, (b) infusing a peritoneal dialysis fluid in an amount of about 1.0 to about 2.0 L into the peritoneal cavity, (c) maintaining a substantially effective osmotic pressure of the peritoneal dialysis fluid in the peritoneal cavity, (d) transferring said peritoneal dialysis fluid to the dialyzer via a liquid pathway using a pump, (e) cleansing the transferred peritoneal dialysis fluid in the extracorporeal dialyzer using a detergent solution provided from the source of detergent solution and (f) reinfusing the cleansed peritoneal dialysis fluid into the peritoneum. These steps are continued during the dialysis. Although the time of dialyzing a patient depends on the status of the patient or the dialysis efficiency of the dialysis fluid, usually it takes about 3 to 8 hours. The velocity of transferring the dialysis fluid, that is, the circulating amount is controlled, but is preferably about 50 to about 200 mL/h. The amount of the detergent solution in the dialyzer is about 100 to about 500 mL/h.

Figure 2:
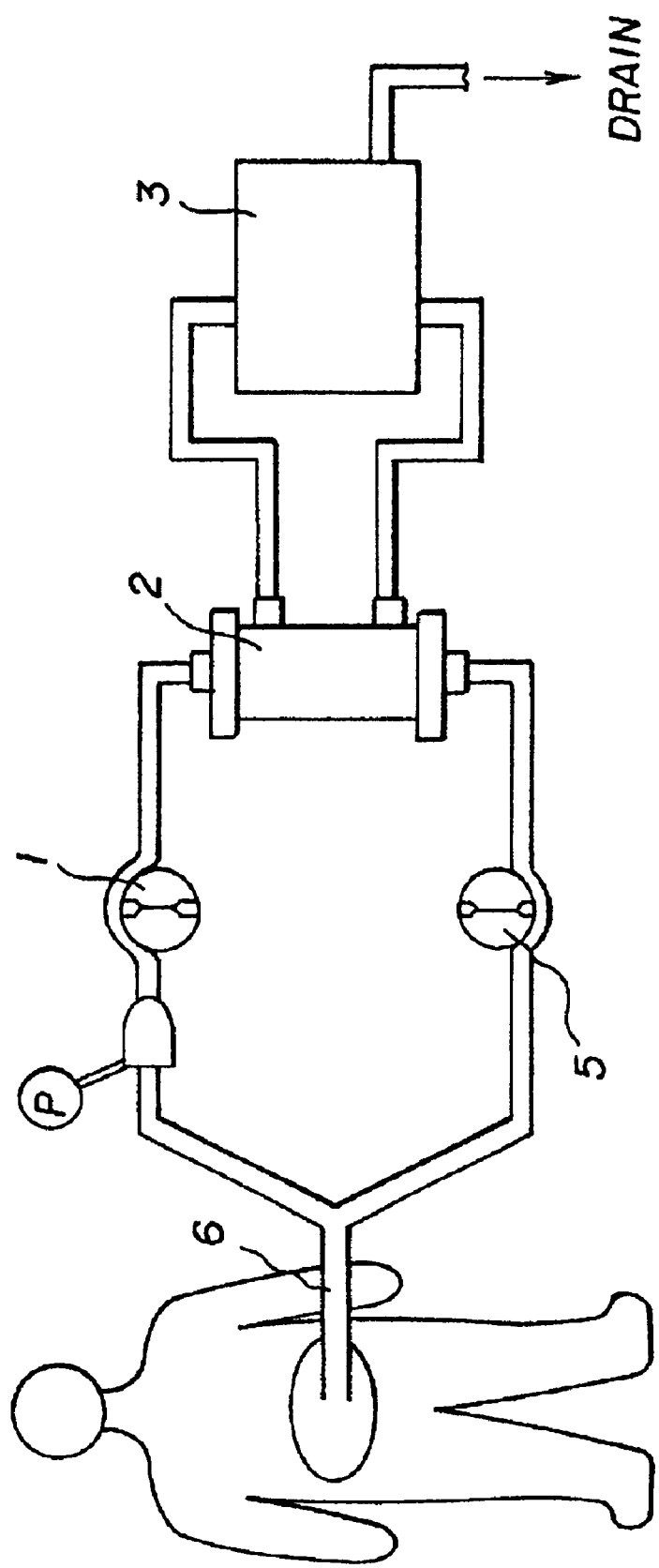
FIG. 2 shows another scheme of continuous recirculating peritoneal dialysis.

In the peritoneal dialysis system illustrated in FIG. 1, a peritoneal dialysis fluid is drained by a pump 1 to an external dialyzer 2 from the peritoneal cavity, is cleansed with a detergent solution transported from a detergent solution supplying apparatus 3 and is returned into the peritoneal cavity, in which procedure as the catheter for dialysis a double lumen catheter 4 is used. Further, in the peritoneal dialyzer shown in FIG. 2, a single lumen catheter 6 as a catheter for dialysis is placed in the peritoneal cavity and the dialysis fluid purified in the external dialyzer 2 is transported back into the peritoneal cavity by a pump 5. The peritoneal system illustrated in FIG. 3 has a reversible pump 7 arranged in the dialysis circuit line and a peritoneal dialysis fluid pooling bag 8 connected to one end of the dialysis circuit line, and the peritoneal dialysis fluid is passed back and forth between the peritoneal cavity and the peritoneal dialysis fluid pooling bag 8.

EXAMPLE 1

A peritoneal dialysis fluid having the following formula was prepared.

| albumin | (%) | 5, 10 or 20 |
|---|---|---|
| sodium ion | (mEq/L) | 132 |
| calcium ion | (mEq/L) | 3.5 |
| magnesium | (mEq/L) | 1.5 |
| chloride ion | (mEq/L) | 102 |
| lactate ion | (mEq/L) | 35 |

Continuous recirculating peritoneal dialysis was carried out on three renal failure dogs using the dialysis system illustrated in FIG. 1. In detail, 662 mL to 946 mL of the above peritoneal dialysis fluid was infused into the peritoneal cavity of these dogs, maintained in the cavity for 6 hours and drained out of the cavity to be cleansed by the detergent solution under a circulating amount of 100 mL/h in the cellulose acetate dialyzer. The dialysate "SOLITA (trade name)" manufactured by Shimizu Pharmaceutical Co., Ltd. as a detergent solution was supplied into the dialyzer under 100 mL/L of flow. After 6 hours of the peritoneal dialysis, the amount of removed water in the dialysis fluid in the peritoneal cavity and the removing ratio of urea were determined. The results were as follows:

TABLE 1

| the concentration of albumin in the dialysis fluid | the amount of removed water | the removing ratio of urea |
|---|---|---|
| 5% | 95 mL | 14.7% |
| 10% | 160 mL | 10.0% |
| 20% | 380 mL | 12.5% |

The concentration of albumin in the drained dialysis fluid after circulating in the peritoneal cavity is determined by a commercially available albumin measurement reagent, Albumin Test Wako(trade name) manufactured by Wako Pure Chemical Industries, Ltd. The results were as follows:

TABLE 2

| the concentration of albumin in the dialysis fluid | The remaining ratio of the concentration of albumin in the drained dialysis fluid |
|---|---|
| 5% | 90% |
| 10% | 84% |
| 20% | 85% |

The peritoneal dialysis fluid of the present invention used for a continuous recirculating peritoneal dialysis system comprises as an osmotic agent a substance which does not substantially permeate through pores of a hollow fiber membrane of an extracorporeal dialyzer. Therefore, supplementing of the osmotic agent is not needed during the dialysis as compared with a conventional osmotic agent like glucose. The peritoneal dialysis fluid enables an efficient and continuous dialysis as well as a cost reduction of the dialysis fluid.

What is claimed is:

1. A method for a continuous recirculating peritoneal dialysis comprising
    i) infusing a peritoneal dialysis fluid in a peritoneal cavity, said fluid comprising
    albumin in an amount of about 20 to about 250 g/L,
    sodium ions in an amount of about 130 to about 140 mEq/L,
    magnesium ions in an amount of about 0.5 to about 2.0 mEq/L,
    calcium ions in an amount of about 3.0 to about 4.5 mEq/L,
    chloride ions in an amount of about 95 to about 110 mEq/L, and
    lactate ions in an amount of about 35 to about 40 mEq/L
    ii) sequentially draining the peritoneal dialysis fluid out of the peritoneal cavity,
    iii) cleansing the peritoneal dialysis fluid through an extracorporeal dialyzer, and
    iv) reinfusing the cleansed peritoneal fluid into the peritoneal cavity.

2. The method for a continuous recirculating peritoneal dialysis as claimed in claim 1, wherein the concentration of albumin is from about 70 to about 150 g/L.

3. The method for a continuous recirculating peritoneal dialysis as claimed in claim 1, wherein the albumin comprises human serum albumin.

4. A method for dialyzing a patient which comprises (a) plating a fluid pathway in a peritoneum of the patient, (b) infusing a peritoneal dialysis fluid comprising
    albumin in an amount of about 20 to about 250 g/L,
    sodium ions in an amount of about 130 to about 140 mEq/L,
    magnesium ions in an amount of about 0.5 to about 2.0 mEq/L,
    calcium ions in an amount of about 3.0 to about 4.5 mEq/L,
    chloride ions in an amount of about 95 to about 110 mEq/L, and
    lactate ions in an amount of about 35 to about 40 mEq/L
    into a peritoneal cavity, (c) sequentially draining the peritoneal dialysis fluid out of the peritoneal cavity, (d) transferring said peritoneal dialysis fluid to an extracorporeal dialyzer which consists of hollow fiber membranes, (e) cleansing the transferred peritoneal dialysis fluid in the dialyzer using a detergent solution and (f) reinfusing the cleansed peritoneal dialysis fluid into the peritoneum.

5. The method as claimed in claim 4, wherein the fluid pathway is a catheter.

6. The method as claimed in claim 4, wherein the extracorporeal dialyzer consists of a hollow fiber membrane having a separation limitation of about 2,000 to about 10,000 daltons.

* * * * *